United States Patent [19]

Shepherd

[11] Patent Number: 4,609,748
[45] Date of Patent: Sep. 2, 1986

[54] NOVEL SILYL REAGENTS

[75] Inventor: Robin G. Shepherd, Maidenhead, England

[73] Assignee: John Wyeth & Brother, Ltd., Maidenhead, England

[21] Appl. No.: 723,772

[22] Filed: Apr. 16, 1985

Related U.S. Application Data

[63] Continuation-in-part of Ser. No. 506,279, Jun. 21, 1983, Pat. No. 4,526,970.

[30] Foreign Application Priority Data

Jun. 25, 1982 [GB] United Kingdom ................. 8218465

[51] Int. Cl.$^4$ ............................................... C07F 7/10
[52] U.S. Cl. ................................................... 556/410
[58] Field of Search ......................................... 556/410

[56] References Cited

FOREIGN PATENT DOCUMENTS 0729212  3/1966  Canada ................................. 556/410

OTHER PUBLICATIONS

Eaborn, Organosilicon Compounds, pp. 219–226 (1960), Butterworths Scientific Publications, London, England.
Schott et al., Z. Chemie, 14 pp. 487–488, (1974).
Watanabe et al., Chemistry Letter-Chem. Soc. Japan, pp. 1173–1176, (1976).

Primary Examiner—Paul F. Shaver
Attorney, Agent, or Firm—Richard K. Jackson

[57] ABSTRACT

The invention provides novel silyl reagents of Formula I $$R^b R^c R^d SiNCY$$

wherein $R^b$ is a branched chain alkyl of 3–10 carbon atoms, cycloalkyl of 4–8 carbon atoms or branched chain aralkyl of 8–12 carbon atoms and $R^c$ and $R^d$ are selected from alkyl of 1–10 carbon atoms, cycloalkyl of 4–8 carbon atoms, aralkyl of 7–12 carbon atoms or aryl with the proviso that $R^c$ and $R^d$ are not the same group as $R^b$, and Y is oxygen or sulphur. A further novel compound tri-isopropylsilyl isothiocyanate is also included. These silyl reagents are useful in preparing tetrahydroquinoline 8-nitriles, amides and thioamides as described in Ser. No. 506,279.

6 Claims, No Drawings

NOVEL SILYL REAGENTS

The invention relates to novel silyl intermediates useful in a new process for preparing fused carbocyclic ring derivatives of pyridine which is the subject of co-pending application Ser. No. 506,279 filed June 21, 1983, now U.S. Pat. No. 4,526,970 granted July 2, 1985. This application is a continuation-in-part of Ser. No. 506,279.

In our United Kingdom Specification No. 1463666 we described a process for preparing tetrahydroquinoline-8-thiocarboxamides, nitriles and carboxamides and related compounds by treating a corresponding sodio, lithio, potassio or magnesium halide derivative with a silyl compound of formula $R_xSi(NCY)_{4-x}$ wherein R is alkyl, aryl or aralkyl, Y is oxygen or sulphur and x has a value from 0 to 3 and subjecting the product to hydrolysis or alcoholysis. The reaction is conducted under anhydrous conditions preferably in an inert solvent for example a hydrocarbon solvent such as benzene, toluene or n-hexane. It is also stated in that patent specification that ethers, including cyclic ethers such as tetrahydrofuran should be avoided.

We have now surprisingly found that ethers can be used as solvents if the silyl reagent is modified to contain selected hydrocarbon groups and furthermore the yields are often better than with the solvents described in UK Specification No. 1463666. Our new process, which is described and claimed in our copending Ser. No. 506,279, can also be used to prepare compounds related to those described in Patent Specification No. 1463666.

Some of the silyl reagents useful in this new process are novel and give particularly good yields.

Accordingly this invention provides a compound of Formula I $$R^bR^cR^dSiNCY$$

wherein $R^b$ is a branched chain alkyl of 3–10 carbon atoms, cycloalkyl of 4–8 carbon atoms, or branched chain aralkyl of 8–12 carbon atoms and $R^c$ and $R^d$ are selected from alkyl of 1–10 carbon atoms, cycloalkyl of 4–8 carbon atoms, aralkyl of 7–12 carbon atoms or aryl with the proviso that $R^c$ and $R^d$ are not the same group as $R^b$, and Y is oxygen or sulphur.

A further compound of the invention is tri-isopropyl-silyl isothiocyanate.

If at least one of $R^b$, $R^c$ and $R^d$ is not t-alkyl then preferably at least two groups $R^b$, $R^c$ and $R^d$ are selected from branched chain alkyl, cycloalkyl or branched chain aralkyl.

Preferably $R^b$ is branched chain alkyl of 3–10 carbon atoms and $R^c$ and $R^d$ are selected from alkyl groups of 1–10 carbon atoms and at least one such group is a tertiary alkyl group eg., t-butyl or t-amyl. Good results have been obtained in the process of Serial No. 506,279 with a silyl compound of Formula I wherein $R^b$ is t-butyl and $R^c$ and $R^d$ are lower alkyl eg., t-butyldimethylsilyl isothiocyanate.

An alkyl group is preferably a lower alkyl group of 1 to 6 carbon atoms which may have a straight or branched chain eg., methyl, ethyl n- and iso-propyl and n-, s- and t-butyl. When $R^c$ and $R^d$ are lower akyl groups they may be any of the values just discussed.

When any of $R^b$, $R^c$ or $R^d$ is a cycloalkyl group such groups having from 4 to 8 carbon atoms in the ring are preferred eg., cyclobutyl, cyclopentyl or cyclohexyl. Such rings may be substituted by alkyl of 1 to 6 carbon atoms.

An aralkyl group may be an arylalkyl group in which the alkyl portion is as described herein for an alkyl group. Preferred aralkyl groups are those having from 7–12 carbon atoms. $R^c$ and $R^d$ when aralkyl may be phenylalkyl, naphthylmethyl or naphthylethyl.

When $R^c$ or $R^d$ is an aryl group it is preferably phenyl or substituted phenyl (substituted by eg. alkyl of 1–6 carbon atoms, alkoxy of 1–6 carbon atoms or trifluoromethyl).

The silyl compounds of Formula I may be prepared by reacting a thiocyanate, such as ammonium thiocyanate, or a cyanate with a silyl halide eg., $R^bR^cR^dSiHal$ where $R^b$, $R^c$ and $R^d$ are as defined above and Hal is chlorine, bromine or iodine.

Preferably $R^c$ and $R^d$ are alkyl radicals at least one and preferably both being n-alkyl radicals.

A particularly preferred compound of Formula I is t-butyldimethylsilyl isothiocyanate.

The compounds of the present invention may be reacted with the tetrahydroquinoline derivatives by the process of Ser. No. 506279 in either solvents eg. dialkyl ethers; wherein the alkyl group has from 1 to 6 carbon atoms, eg. diethyl ether or a cyclic ether such as tetrahydrofuran or dioxane. The solvents described in UK Patent Specification No. 1463666 eg. hydrocarbons such as benzene and toluene may also be used.

Mixtures of solvents may be used eg. an ether/hydrocarbon such as tetrahydrofuran/hexane.

The following Example illustrates the invention.

EXAMPLE

PREPARATION OF SILYL ISOTHIOCYANATES

General Method

Ammonium thiocyanate (1.1 molar equivalents) in cyclohexane (100 ml) was refluxed with stirring under a Dean-Stark apparatus until water had been removed. The suspension was cooled and treated with a silyl chloride (50 g) and the mixture was heated at reflux with stirring until the reaction was complete (usually 24 hours). Precipitated ammonium chloride was removed by filtration and the product purified by distillation. In this manner were prepared the following:

| Silyl chloride | Silylisothiocyanate | bp/mm | Yield |
| --- | --- | --- | --- |
| (a) t-BuMe$_2$SiCl | t-BuMe$_2$SiNCS | 62°/16 | 93% |
| (b) i-Pr$_3$SiCl | i-Pr$_3$SiNCS | 126°/15 | 71% |

What is claimed is:

1. A compound of Formula I $$R^bR^cR^dSiNCS$$

wherein $R^b$ is a branched chain alkyl of 3-10 carbon atoms, cycloalkyl of 4-8 carbon atoms, or branched chain aralkyl of 8-12 carbon atoms and $R^c$ and $R^d$ are selected from alkyl of 1-10 carbon atoms, cycloalkyl of 4-8 carbon atoms, aralkyl of 7-12 carbon atoms or aryl with the proviso that $R^c$ and $R^d$ are not the same group as $R^b$.

2. A compound of Formula I, as claimed in claim 1, wherein $R^c$ and $R^d$ are both alkyl groups of 1-6 carbon atoms.

3. A compound of Formula I, as claimed in claim 2, wherein $R^c$ and $R^d$ are both n-alkyl groups.

4. A compound as claimed in claim 1, wherein $R^b$ is t-butyl.

5. t-Butyldimethylsilyl isothiocyanate.

6. Tri-isopropylsilyl isothiocyanate.

* * * * *